(12) United States Patent
Nikitina et al.

(10) Patent No.: US 9,339,640 B2
(45) Date of Patent: May 17, 2016

(54) CONNECTOR FOR MULTIPLE SIZES OF TUBING

(75) Inventors: Ludmila Nikitina, Raleigh, NC (US); Brett Franks, San Diego, CA (US); James Fentress, Creedmoor, NC (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 13/026,132

(22) Filed: Feb. 11, 2011
(Under 37 CFR 1.47)

(65) Prior Publication Data
US 2012/0209252 A1 Aug. 16, 2012

(51) Int. Cl.
*A61M 39/10* (2006.01)
*F16L 13/10* (2006.01)

(52) U.S. Cl.
CPC .............. *A61M 39/10* (2013.01); *F16L 13/103* (2013.01); *Y10T 137/0402* (2015.04)

(58) Field of Classification Search
CPC ................ A61M 39/10; A61M 39/12; A61M 2039/1077; F16L 13/103; Y10T 137/0402
USPC .......... 604/284, 533–539; 285/239, 240, 260, 285/332, 399, 423; 137/798, 799
See application file for complete search history.

(56) References Cited

U.S. PATENT DOCUMENTS

| | | | | |
|---|---|---|---|---|
| 3,406,685 | A * | 10/1968 | May ......................... | 604/164.11 |
| 4,000,740 | A * | 1/1977 | Mittleman ................... | 604/86 |
| 4,693,710 | A | 9/1987 | McCool | |
| 4,875,719 | A * | 10/1989 | Mylett ....................... | 285/239 |
| 5,222,486 | A | 6/1993 | Vaughn | |
| 5,286,067 | A * | 2/1994 | Choksi ....................... | 285/38 |
| 5,292,305 | A * | 3/1994 | Boudewijn et al. ......... | 604/43 |
| 7,455,325 | B2 * | 11/2008 | Mejlhede et al. .......... | 285/286.1 |
| 7,488,008 | B2 | 2/2009 | Hawkins | |
| 7,611,503 | B2 * | 11/2009 | Spohn et al. .............. | 604/533 |
| 2004/0073192 | A1 | 4/2004 | Flament-Garcia et al. | |
| 2007/0060898 | A1 | 3/2007 | Shaughnessy et al. | |
| 2007/0129705 | A1 * | 6/2007 | Trombley et al. .......... | 604/523 |
| 2008/0065023 | A1 | 3/2008 | Kennard | |
| 2008/0183153 | A1 * | 7/2008 | Enns .......................... | 604/533 |
| 2011/0251596 | A1 * | 10/2011 | Kim et al. .................. | 604/533 |

FOREIGN PATENT DOCUMENTS

EP 1705414 A1 9/2006
FR 2522969 A1 9/1983

OTHER PUBLICATIONS

"Solvent bonding" definition. Royal DSM. <http://www.dsm.com/en_US/html/dep/solvent_bonding.htm>.*
"Solvent bonding" definition. Bayer Material Science. <http://www.bayermaterialsciencenafta.com/checklist/solvent_bonds.html>.*
International Search Report and Written Opinion for PCT/US2012/024767 mailed Oct. 23, 2012.
Extended European Search Report in EP Application No. 12744262.2/Patent No. 2673022 dated Aug. 5, 2014.

* cited by examiner

*Primary Examiner* — Kami A Bosworth
(74) *Attorney, Agent, or Firm* — McDermott Will & Emery LLP

(57) ABSTRACT

A body is disclosed that includes a tubular portion with an internal bore and an external surface and a first opening wherein the internal bore terminates at the first opening. The body has a second opening and a fluid passage extending through the body from the internal bore to the second opening. The internal bore is configured to couple to an external surface of a first tube and the external surface is configured to couple to an internal surface of a second tube.

19 Claims, 5 Drawing Sheets

CONNECTOR FOR MULTIPLE SIZES OF TUBING

BACKGROUND

1. Field

The present disclosure generally relates to systems and methods of joining tubing and, in particular, fittings that can join to a range of sizes of tubing.

2. Description of the Related Art

One method of transferring fluids from one location to another is through fluid conduits that are referred to by a variety of names including tubing, pipe, piping, hoses, and lines. The name is frequently associated with the diameter of the fluid conduit. fluid conduit that is flexible, made of a plastic, and having an outer diameter on the order of a few centimeters or less is commonly called tubing although this varies across industries. It is common to attach a coupling or fitting to one or both ends of the fluid conduit to enable easier attachment to fluid containers or other fluid-handling elements or to create more complex fluid transfer systems. Fittings are commonly sized to match the inside or outside diameter of the fluid conduit, and each size of fluid conduit typically requires a unique size of fitting to provide the proper fit between the fluid conduit and the fitting.

In the medical field, fluids are frequently administered as infusions. The container holding the medical fluid, such as a flexible intravenous (IV) bag, is connected to an infusion device, such as an IV needle, by a disposable IV set comprising tubing having one or more fittings. IV sets may also have intermediate ports or connection points where additional fluid containers may be connected to introduce or withdraw fluid. The tubing is connected to the fittings by one or more of mechanical attachment, such as a barbed fitting that is inserted into the interior of the tubing, and bonding, such as a solvent weld between an internal pocket of the fitting and the exterior surface of the tubing. One of the challenges of fabricating IV sets is that tubing comes in a wide variety of sizes and the availability of a specific size of tubing may be intermittent, sometimes leading to unintended shutdowns of production for lack of the compatible fittings and tubing.

SUMMARY

To address at least some of the above mentioned challenges, it is desirable to provide a single fitting that connects to a range of sizes of tubing.

In certain embodiments, a fitting is disclosed that comprises a body comprising a tubular portion with an internal bore and an external surface and a first opening wherein the internal bore terminates at the first opening and the body further comprises a second opening, and a fluid passage extending through the body from the internal bore to the second opening, wherein the internal bore is configured to couple to an external surface of a first tube and the external surface is configured to couple to an internal surface of a second tube.

In certain embodiments, a method of assembling a fitting and a flexible tube is disclosed. The method comprises the steps of selecting a rigid fitting and a flexible tube having either an external surface that is configured to couple to an internal surface of a tubular portion of the rigid fitting or an internal surface that is configured to couple to an external surface of the tubular portion of the rigid fitting, coupling the outer surface of the flexible tube to the internal surface of the tubular portion of the rigid fitting when the external surface of the flexible tube is configured to couple to the internal surface of the tubular portion of the rigid fitting, and coupling the internal surface of the flexible tube to the external surface of the tubular portion of the rigid fitting when the internal surface of the flexible tube is configured to couple to the external surface of the tubular portion of the rigid fitting.

In certain embodiments, an IV set is disclosed that comprises a fitting comprising a body comprising a tubular portion with an internal bore and an external surface and a first opening wherein the internal bore terminates at the first opening and the body further comprises a second opening and a fluid passage extending through the body from the internal bore to the second opening wherein the internal bore is configured to couple to an external surface of a first tube and the external surface is configured to couple to an internal surface of a second tube, and one or more pieces of flexible tubing, wherein either the external surface of at least one piece of the flexible tubing is coupled to the internal bore of the tubular portion of the body of the fitting or the internal surface of at least one piece of the flexible tubing is coupled to the external surface of the tubular portion of the body of the fitting.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The systems and methods disclosed herein disclose a fitting configured to join to multiple sizes of tubing and methods of assembling the fitting with the various sizes of tubing.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
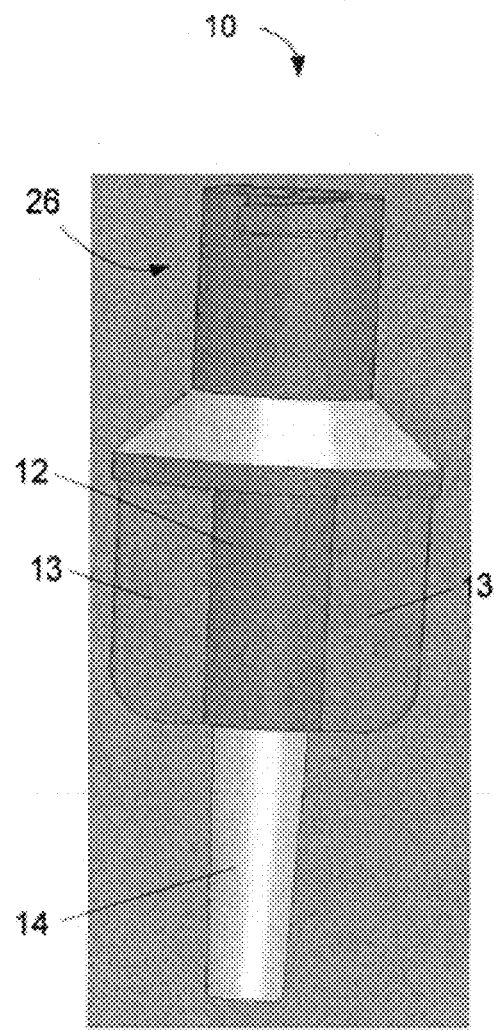
FIG. 1 depicts an exemplary embodiment of a fitting configured to accept multiple sizes of flexible tubing according to certain aspects of the present disclosure.

FIG. 1 depicts an exemplary embodiment of a fitting 10 configured to accept multiple sizes of flexible tubing (not shown) according to certain aspects of the present disclosure. The fitting 10 has a body 12 that comprises a tubular portion 14 at one end and, in this example, a female luer connector 26 at the other end. Body 12 also comprises two wing tabs 13 that provide improved gripping capability for nurses using the fitting 10.

Figure 2:
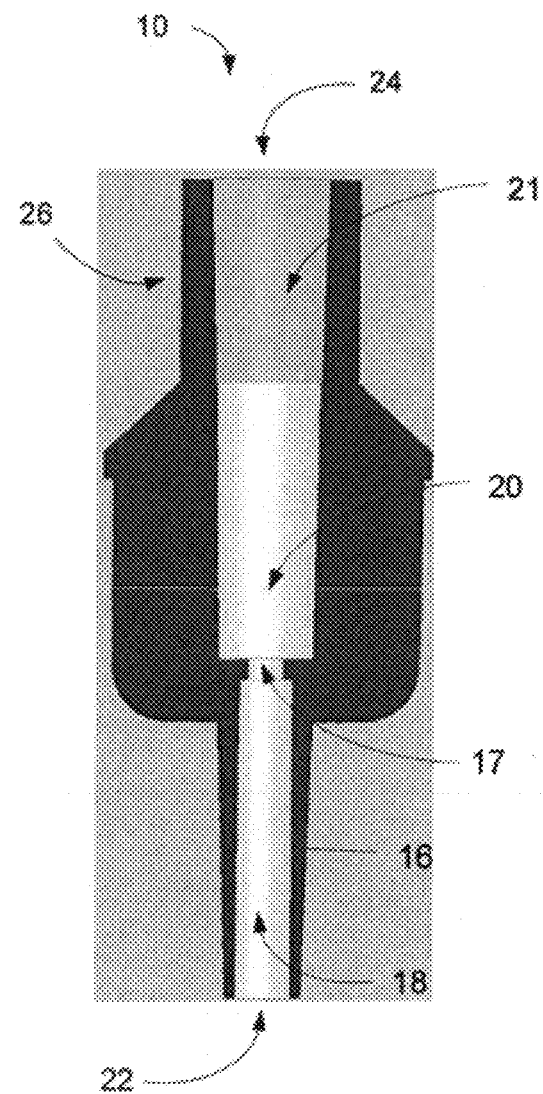
FIG. 2 depicts a cross-section of the fitting of FIG. 1 according to certain aspects of the present disclosure.

FIG. 2 depicts a cross-section of the fitting 10 of FIG. 1 according to certain aspects of the present disclosure. The tubular portion 14 comprises an internal bore 18 and an external surface 16. In this example, internal bore 18 is an approximate cylinder of constant cross-section and the external surface 16 is tapered to form a truncated cone that is approximately concentric with internal bore 18. In other embodiments, the external surface 16 may be approximately cylindrical with a constant cross-section. The body 12 has a first opening 22 at the tip of the tubular portion 14, wherein the internal bore 18 connects with the first opening 22, and a second opening 24 at the end of the body 12 opposite the tubular portion 14. There is a restriction 17 at the end of internal bore 18 that serves as a stop for the insertion of tubing into the internal bore 18, where restriction 17 has a diameter that is smaller than the diameter of internal bore 18. The body 12 can be seen to have a fluid passage 20/21 that passes through the body 12 from the internal bore 18 to the second opening 24, where fluid passage 21, in this example, is tapered and configured to mate with the tip of a standard male Luer fitting.

Tubing having an inner diameter of greater than 0.100 inches is typically considered "macrobore" and is expanded on a standard tubing expander prior to being slipped over a connector such as external surface 16. Tubing with an inner diameter of less than 0.100 inches, and particularly tubing having an outer diameter of approximately 0.079 inches, is considered "smallbore" or "microbore" and is bonded into a tubing pocket such as internal bore 18.

Figure 3A:
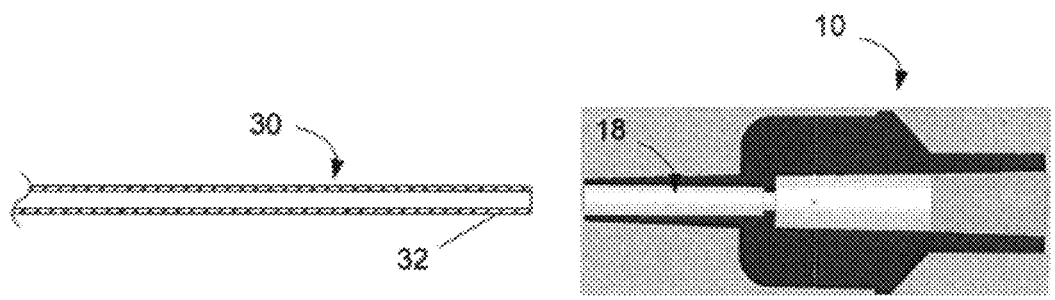
FIGS. 3A-3B depict assembly of the fitting of FIG. 1 with smallbore tubing according to certain aspects of the disclosure.
Figure 3B:
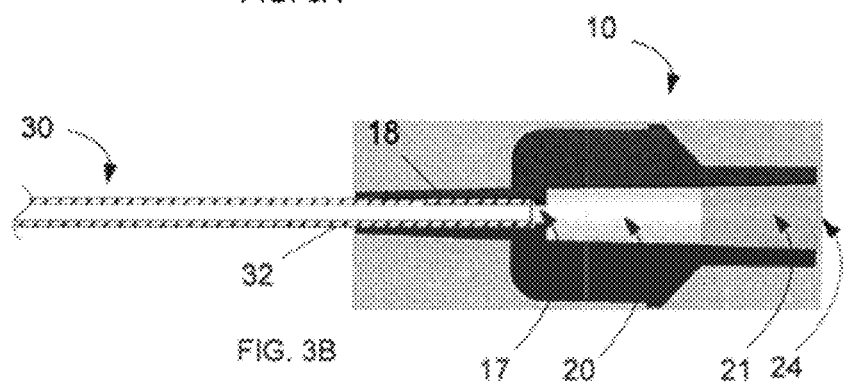

FIGS. 3A-3B depict assembly of the fitting 10 of FIG. 1 with smallbore tubing 30 according to certain aspects of the disclosure. FIG. 3A shows an end of smallbore tubing 30 having an external surface 32 positioned proximate to the internal bore 18 of fitting 10. The diameter of the internal bore 18 is sized to fit the outside diameter of smallbore tubing 30. In certain embodiments, the outer diameter of smallbore tubing is approximately 0.079 inches. In this example, the inside diameter of internal bore 18 is slightly larger than the diameter of external surface 32 such that an adhesive or solvent, such as cyclohexanone, may be used to retain smallbore tubing 30 in internal bore 18. In other embodiments, the diameter of the internal bore 18 may be nominally the same as that of external surface 32. In other embodiments, internal bore 18 may have retention features (not shown) that mechanically retain smallbore tubing 30 in the internal bore 18 without adhesive. FIG. 3B depicts fitting 10 and smallbore tubing 30 wherein a portion of tubing 30 has been inserted into the internal bore 18 until the smallbore tubing 30 contacts the restrictor 17. Once assembled as seen in FIG. 3B, fluid is able to flow through smallbore tubing 30 into the restrictor 17 and then into fluid passages 20/21 to opening 24. If fitting 10 is mated with another connector (not shown) in fluid passage 21, a fluid connection exists from smallbore tubing 30 to the internal flow channel of the mated connector.

Figure 4A:
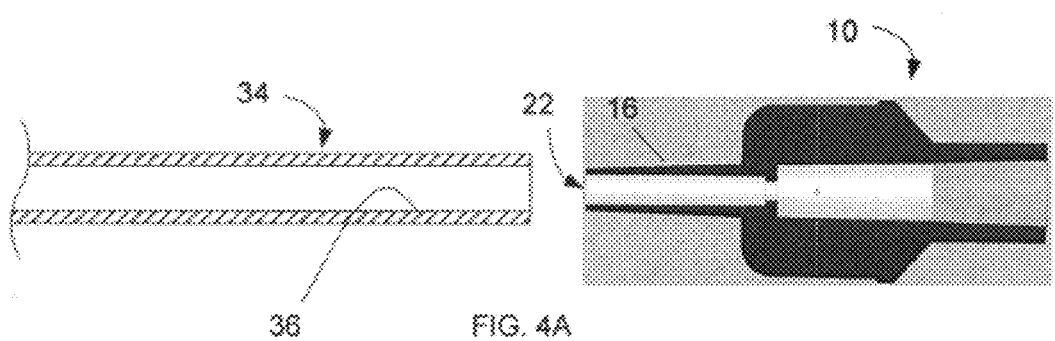
FIGS. 4A-4B depict assembly of the fitting of FIG. 1 with macrobore tubing according to certain aspects of the disclosure.
Figure 4B:
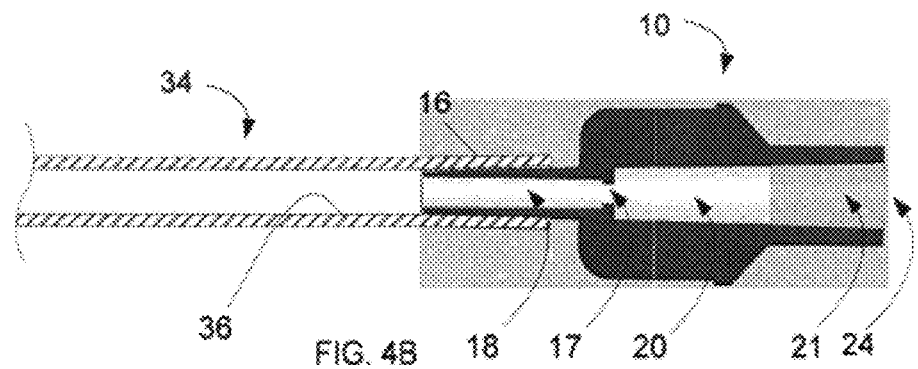

FIGS. 4A-4B depict assembly of the fitting 10 of FIG. 1 with a macrobore tubing 34 according to certain aspects of the disclosure. FIG. 4A shows an end of a piece of macrobore tubing 34 having an internal surface 36 positioned proximate to the tubular portion 16 of fitting 10. It can be seen that, in this example, the diameter of the internal surface 36 is approximately equal to the diameter of the external surface 16 at opening 22. In certain other embodiments, the inside diameter of internal surface 36 is smaller than the diameter of the external surface 16 at opening 22 and requires forming by a secondary tool (not shown) to increase the inside diameter of large bore tubing 34 to fit over the external surface 16 of fitting 10. In certain other embodiments, the inner diameter of the macrobore tubing 34 is approximately 0.100 inches. FIG. 4B depicts the assembled condition of large bore tubing 34 and fitting 10 wherein a portion of macrobore tubing 34 is over external surface 16 of fitting 10. In this example, a lubricant (not shown) such as isopropyl alcohol has been applied to the internal surface 36 of large bore tubing 34 prior to assembly to aid in sliding macrobore tubing 34 over external surface 16, whereupon the lubricant will evaporate after assembly leaving sufficient friction between internal surface 36 and external surface 16 to retain macrobore tubing 34 on fitting 10. In certain embodiments, a solvent (not shown) such as cyclahexanone is applied to the external surface 16 prior to assembly such that the material of the external surface 16 is softened and will conform to the internal surface 36 after assembly, wherein the solvent will evaporate and leave the hardened material of external surface 16 in intimate contact with the internal surface 36 of large bore tubing 34. In certain other embodiments, an adhesive is applied to the external surface 16 prior to assembly such that large bore tubing 34 is bonded to fitting 10 after the adhesive cures. Once assembled as seen in FIG. 4B, fluid is able to flow through macrobore tubing 34 into the internal bore 18, through restrictor 17, and then into fluid passages 20/21 to opening 24. If fitting 10 is mated with another connector (not shown) in fluid passage 21, a fluid connection exists from macrobore tubing 34 to the internal flow channel of the mated connector.

Figures 5, 6:
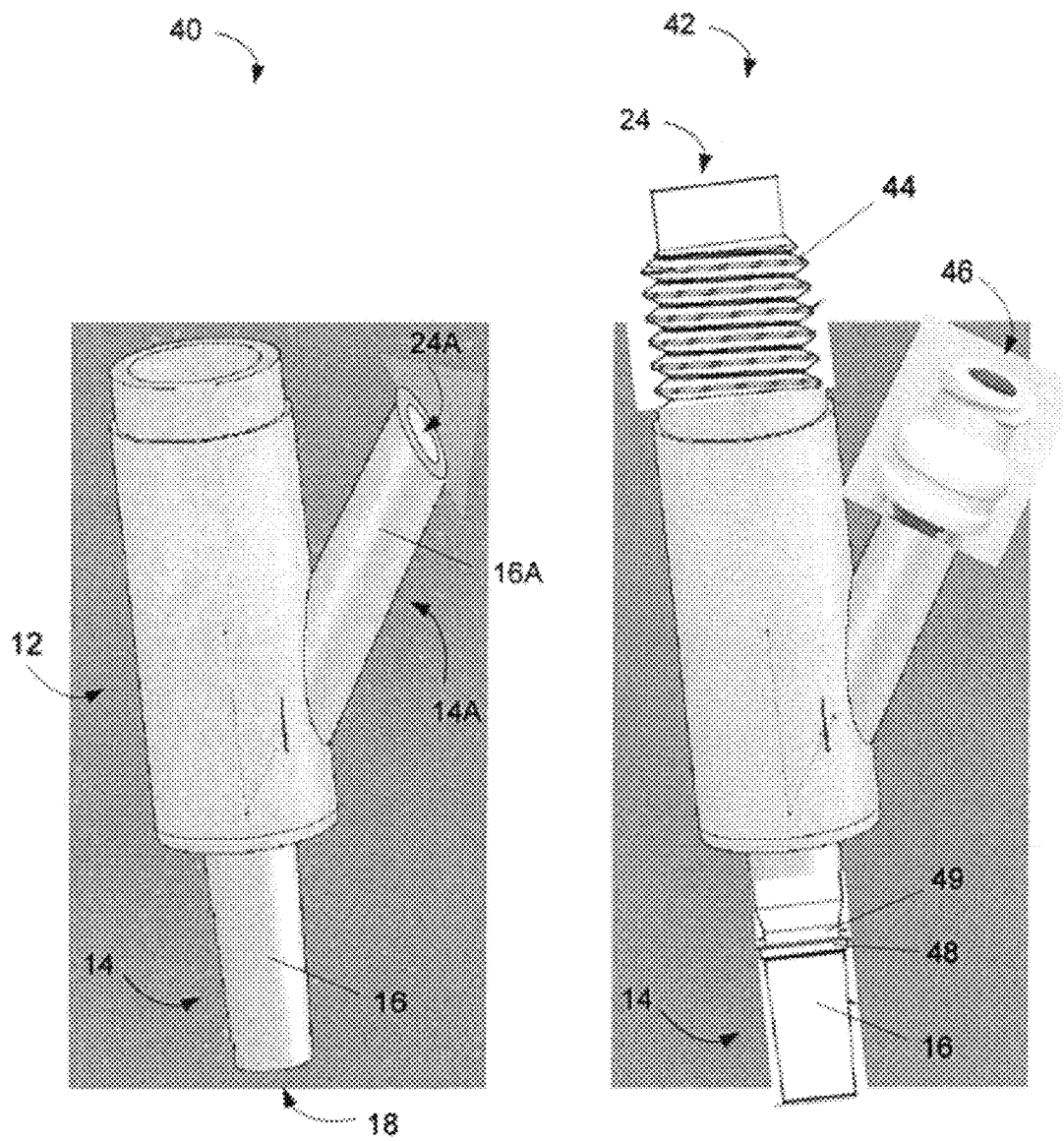
FIG. 5 depicts a Y-fitting according to certain aspects of the disclosure.
FIG. 6 depicts another embodiment of a Y-fitting according to certain aspects of the disclosure.

FIG. 5 depicts a Y-fitting 40 according to certain aspects of the disclosure. In this example, a first piece of flexible tubing (not shown) is to be bonded to a bottom tubular portion 14 and a second piece of flexible tubing (not shown) is to be bonded to a side tubular section 14A having an external surface 16A and a second opening 24A. It can be seen that tubular portion 14A is cut off at an angle at the location of opening 24A to aid in starting the internal surface of macrobore tubing 34 (such as shown in FIG. 4A) over external surface 16A.

FIG. 6 depicts another embodiment of a Y-fitting 42 according to certain aspects of the disclosure. In this example the opening 24A of FIG. 5 has been replaced with a needleless connector 46 that is, in this example, a female Luer connector with a sealing plug. Body 12 comprises a mechanical attachment element 44 under opening 24, such that fitting 42 can be attached to another fluid device (not shown) having a threaded port. In this example, the tubular portion 14 comprises a ridged ring 48 encircling external surface 16, such that the ridged ring 48 will mechanically retain large bore tubing 34 in place after assembly. In certain embodiments, the ridged ring 48 is a barb having an inclined surface that connects to the external surface 16 and then slopes outward to an increased diameter, further having a ring of reduced diameter 49 immediately adjacent to the barb 48 such that the stretched material of macrobore tubing 34 will contract over the reduced diameter 49, further enhancing the retention ability of barb 48.

Figure 7:
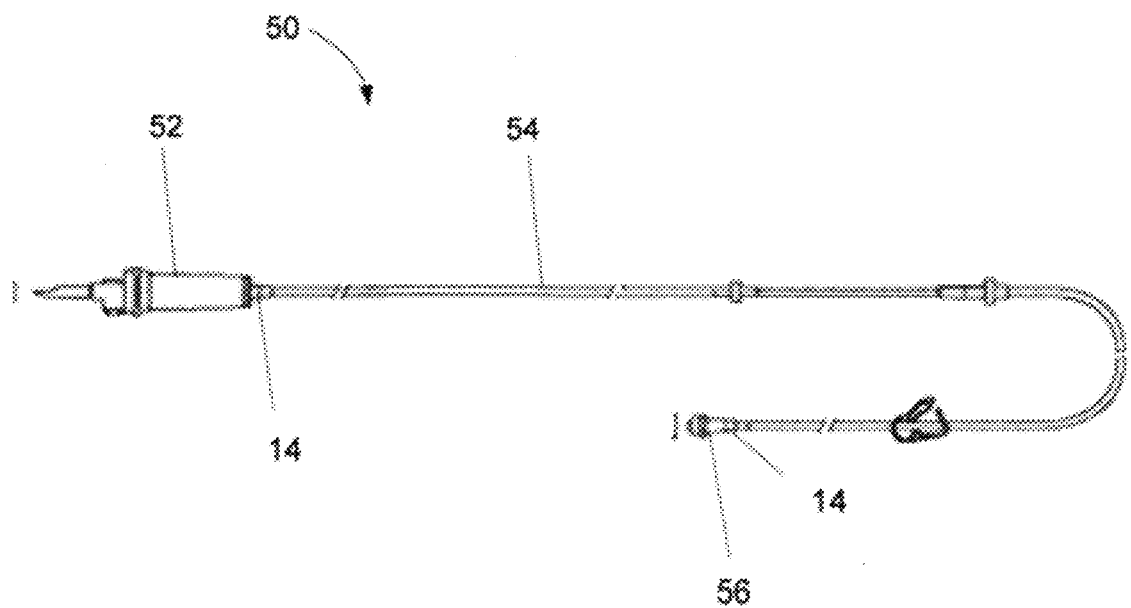
FIG. 7 depicts an IV set according to certain aspects of the disclosure.

FIG. 7 depicts an IV set 50 according to certain aspects of the disclosure. The IV set 50 comprises a standard bag spike 52, such as is normally used to establish a connection to a standard IV bag (not shown), wherein bag spike 52 comprises a tubular portion 14 similar to that of FIGS. 1 and 2. In other words, the tubular portion 14 of bag spike 52 has an internal bore 18 configured to receive smallbore tubing 30 and a tapered external surface 16 configured to receive macrobore tubing 34. The IV set 50 further comprises connector 56 that also comprises a tubular portion 14 also having an internal bore 18 and a tapered external surface 16. This enables IV set 50 to be constructed from a variety of tubing sizes using a single set of bag spike 52 and fitting 56.

Figure 8:
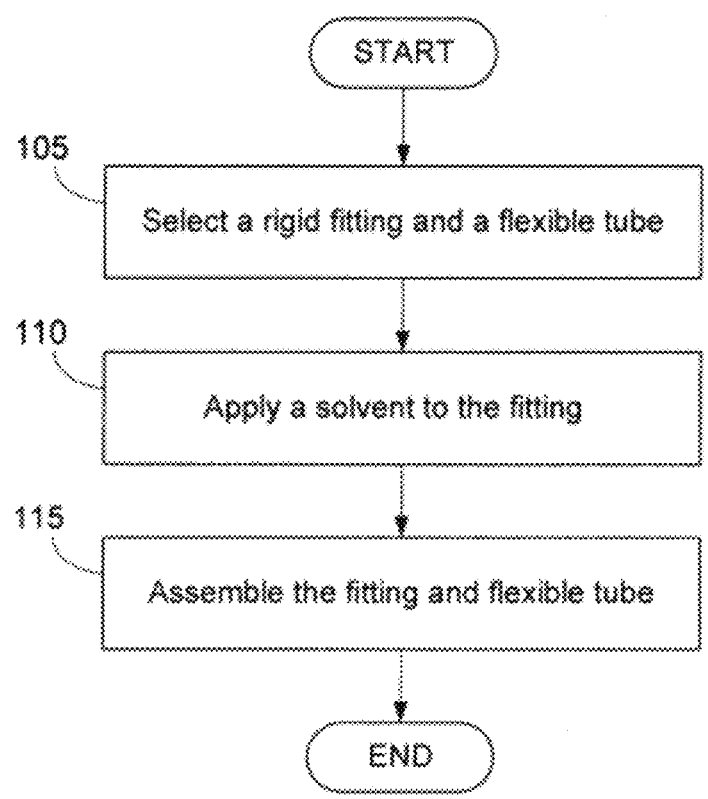
FIG. 8 is a flowchart of a method of attaching flexible tubing to the fitting according to certain aspects of the disclosure.

FIG. 8 is a flowchart of a method of attaching flexible tubing 30/34 to the fitting 10 according to certain aspects of the disclosure. The method begins in step 105 by selecting a rigid fitting 10 and a flexible tubing 30/34 that is either the flexible tubing 30 having an external surface 32 that fits within the internal bore 18 of fitting 10 or the flexible tubing 34 having an internal surface 36 that will fit over the external surface 16 of fitting 10. In certain other embodiments, the relative size of the respective feature 32/36 of the tubing 30/34 and the size of the respective feature 18/16 of fitting 10 will have sufficient clearance for an adhesive. In step 110, a solvent is applied to the feature 18/16 of fitting 10. In certain embodiments, the solvent is applied to the respective feature 32/36 of the tubing 30/34. In certain other embodiments, an adhesive is applied to one or both the feature 18/16 of fitting 10 and the respective feature 32/36 of the tubing 30/34. In certain other embodiments, the lubricant is applied to one or both of the feature 18/16 of fitting 10 and the respective feature 32/36 of the tubing 30/34. In step 115, the prepared fitting 10 and tubing 30/34 are assembled and the solvent allowed to evaporate. After the solvent has evaporated, the process is complete.

It can be seen that the disclosed embodiments of the fitting 10 provide an ability to use either small bore tubing 30 or large bore tubing 34 with a single size of fitting 10. This simplifies the stocking of parts for production of fluid transfer systems such as IV sets using this type of fitting, reduces the chance of a production shutdown for lack of parts, reduces cost by purchasing a single SKU in larger quantities than two fittings each configured for a single size of tubing, and reduces the chance of an assembly error of using the wrong fitting.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A fitting comprising:
a body comprising a tubular portion comprising a length, an internal bore, an external surface, a conical portion, a winged tab, and a tip comprising a first opening, the internal bore having a constant first diameter and extending from the first opening to a restriction at an internal end of the internal bore, the external surface comprising a truncated cone with a second diameter at the tip and increasing in diameter over the length of the tubular portion, the body further comprising a second opening having a third diameter and tapering along its length to a lesser fourth diameter, the conical portion extending from a point between the second opening and the restriction and increasing in cross-section along its length toward the restriction, the winged tab protruding from the external surface and extending from the conical portion to a point between the first opening and the restriction; and
a fluid passage extending through the body from the internal end of the internal bore to the second opening, wherein the restriction comprises a passage having a diameter that is less than the first and fourth diameters.

2. The fitting of claim 1, wherein the first diameter is selected to accept within the internal bore a smallbore tube having an outside diameter of 0.079 inches and the second diameter is selected to accept over the external surface a macrobore tube having an inside diameter of 0.100 inches.

3. The fitting of claim 1, wherein the second opening comprises a portion configured to sealingly mate with a Luer-connector.

4. The fitting of claim 1, wherein the body comprises a material that is responsive to a solvent that softens the material such that the body will conform to either a smallbore tube or a macrobore tube when the fitting is assembled with either the smallbore tube or the macrobore tube after the solvent has been applied to the body.

5. The fitting of claim 4, wherein the solvent is cyclohexanone.

6. The fitting of claim 1, wherein the body comprises a material that is responsive to a glue that, when the fitting is assembled with either a smallbore tube or a macrobore tube, adheres to the tube and to the body.

7. The fitting of claim 1, wherein the internal bore is configured to accept and be sealingly bonded to a smallbore tube having an outside diameter of less than the first diameter within the internal bore, and the truncated cone is configured to accept and be sealingly bonded to a macrobore tube having an inside diameter of greater than the second diameter over the external surface.

8. A method of assembling a fitting and a flexible tube, the method comprising the steps of:
selecting a fitting as set forth in claim 1 and a flexible tube having either an external surface that is configured to couple to an internal surface of the tubular portion of the fitting or an internal surface that is configured to couple to the external surface of the tubular portion of the fitting;
coupling the outer surface of the flexible tube to the internal surface of the tubular portion of the fitting when the external surface of the flexible tube is configured to couple to the internal surface of the tubular portion of the fitting; and
coupling the internal surface of the flexible tube to the external surface of the tubular portion of the fitting when the internal surface of the flexible tube is configured to couple to the external surface of the tubular portion of the fitting.

9. The method of claim 8, wherein:
the step of coupling the outer surface of the flexible tube to the internal surface of the tubular portion of the fitting comprises application of a volatile lubricant to either or both of the outer surface of the flexible tube or the internal surface of the tubular portion of the fitting; and
the step of coupling the internal surface of the flexible tube to the external surface of the tubular portion of the fitting comprises application of a volatile lubricant to either or both of the internal surface of the flexible tube or the external surface of the tubular portion of the fitting.

10. The method of claim 9, wherein the volatile lubricant is isopropyl alcohol.

11. The method of claim 8, wherein:
the step of coupling the outer surface of the flexible tube to the internal surface of the tubular portion of the fitting comprises application of a solvent to either or both of the outer surface of the flexible tube or the internal surface of the tubular portion of the fitting; and
the step of coupling the internal surface of the flexible tube to the external surface of the tubular portion of the fitting comprises application of a solvent to either or both of the internal surface of the flexible tube or the external surface of the tubular portion of the fitting.

12. The method of claim 11, wherein the solvent is cyclohexanone.

13. The method of claim 8, wherein:
the step of coupling the outer surface of the flexible tube to the internal surface of the tubular portion of the fitting comprises application of an adhesive to either or both of the outer surface of the flexible tube or the internal surface of the tubular portion of the fitting; and
the step of coupling the internal surface of the flexible tube to the external surface of the tubular portion of the fitting comprises application of an adhesive to either or both of the internal surface of the flexible tube or the external surface of the tubular portion of the fitting.

14. An intravenous (IV) set comprising:
a fitting comprising:
a body comprising a tubular portion comprising a length, a first internal bore, an external surface, a conical portion, a winged tab, and a tip comprising a first opening, the internal bore having a constant first diameter and extending from the first opening to a restriction at an internal end of the internal bore, the external surface comprising a truncated cone with a second diameter at the tip and increasing in diameter over the length of the tubular portion, the body further comprising a Luer connector with a second opening having a second internal bore with a third diameter and tapering along its length to a lesser fourth diameter, the conical portion extending from a point between the second opening and the restriction and increasing in cross-section along its length toward the restriction, the winged tab protruding from the external surface and extending from the conical portion to a point between the first opening and the restriction, wherein the restriction comprises a passage having a diameter that is less than the first and fourth diameters; and
a fluid passage extending through the body from the internal end of the internal bore to the second opening; and
a tube comprising one of a smallbore tube partially disposed within and sealingly bonded to the internal bore and a macrobore tube partially disposed over and sealingly bonded to the external surface of the tubular portion of the body of the fitting.

15. The IV set of claim 14, wherein:
the first diameter is selected to accept within the internal bore a smallbore tube having an outside diameter of 0.079 inches and the second diameter is selected to accept over the external surface a macrobore tube having an inside diameter of 0.100 inches; and
the tube is one of a smallbore tube having an outside diameter of 0.079 inches and a macrobore tube having an inside diameter of 0.100 inches.

16. The IV set of claim 14, wherein the Luer connector comprises a female Luer fitting.

17. The IV set of claim 14, wherein:
the body comprises a material that is responsive to a solvent that softens the material; and
the fitting was assembled with either the smallbore tube or the macrobore tube after the solvent had been applied to the body.

18. The IV set of claim 17, wherein the solvent is cyclohexanone.

19. The IV set of claim 14, further comprising a glue that adheres to the tube and to the body, wherein either the smallbore tube or the macrobore tube was assembled with the fitting after the glue was applied to one of the tube and the body.

* * * * *